United States Patent [19]

Patterson

[11] Patent Number: 4,584,014
[45] Date of Patent: Apr. 22, 1986

[54] ETHYLIDENEAMINOOXYACETIC ACIDS AND ESTERS

[75] Inventor: Dennis R. Patterson, North Wales, Pa.

[73] Assignee: Rohm and Haas Company, Philadelphia, Pa.

[21] Appl. No.: 626,945

[22] Filed: Jul. 2, 1984

[51] Int. Cl.$^4$ .................. A01N 37/00; C07C 101/02; C07C 109/106
[52] U.S. Cl. .................. 71/113; 260/501.16; 260/501.17; 560/35; 560/125; 560/145; 560/168; 562/440; 562/507; 562/560; 71/105; 71/106; 71/111; 71/115; 558/398; 558/431; 558/442; 558/441; 558/422; 558/414
[58] Field of Search .................. 560/35, 125, 145, 168; 562/440, 507, 560; 260/465 D, 465.4, 464, 501.16, 501.17; 71/105, 106, 111, 113, 115

[56] References Cited

U.S. PATENT DOCUMENTS

| | | | |
|---|---|---|---|
| 2,470,083 | 5/1949 | Hartung | 562/560 |
| 4,117,154 | 9/1978 | Stetter | 560/168 |
| 4,329,488 | 5/1982 | Frater et al. | |
| 4,425,360 | 1/1984 | Wolff | 560/168 |

OTHER PUBLICATIONS

Schumann, J. Med. Pharm. Chem., 5, pp. 464–477 (1962).
Icli, Siddik et al., "Application of NMR Spectroscopy of Chiral Association Complexes", Org. Mag. Res., vol. 20, No. 3, pp. 145–150 (1982).
Chem. Abstracts, 77:139518h (1972).
Chem. Abstracts, 63:5523(b) (1965).

Primary Examiner—Michael L. Shippen

[57] ABSTRACT

Compounds of the formula

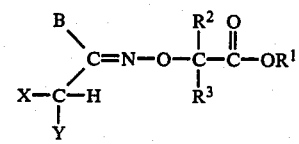

wherein $R^1$ is hydrogen, alkyl, cycloalkyl, phenylalkyl, alkoxyalkyl, alkoxyaryl, aryl or an agronomically acceptable cation; $R^2$ and $R^3$ are each independently hydrogen, optionally substituted alkyl, optionally substituted cycloalkyl, optionally substituted phenylalkyl, carboxy, alkoxycarbonyl or phenyl group; X is hydrogen, fluoro, bromo, chloro or iodo atom; Y is a hydrogen, fluoro, bromo, chloro, iodo, alkyl, cycloalkyl, carboxy, alkoxycarbonyl, phenylalkyl, alkenyl and alkynyl group, wherein the alkyl, cycloalkyl, phenylalkyl and phenyl group may have up to three optional substituents; and B is hydrogen, carboxy, alkoxycarbonyl, methylene ($-CH_2R^4$) or $CZZ^1Z^2$ group wherein $R^4$ is an alkyl or alkenyl group and Z, $Z^1$ and $Z^2$ are each independently a hydrogen, fluoro, bromo, chloro or iodo atom, provided that Z, $Z^1$, $Z^2$, X and Y are not all hydrogens.

13 Claims, No Drawings

ETHYLIDENEAMINOOXYACETIC ACIDS AND ESTERS

FIELD OF INVENTION

This invention relates to novel compounds which show activity as herbicides, to novel herbicidal compositions which contain these compounds and to new methods of controlling weeds with these herbicidal compounds.

BACKGROUND OF THE INVENTION

Various ethylideneaminooxyacetic acids and their esters are generally known. For example, (±)-isopropylideneaminooxypropionic acid is useful as a starting material for the preparation of 2-(2,4,5,7-tetra-nitrofluoren-9-ylideneaminooxy)propionic acid methyl esters; Org. Mag. Res., 20, pp. 145–150 (1982); propionic acid esters, including 2-[[(1-mono or dimethylethylidene)amino]oxy]-propanoic acid and its methyl ester are useful as intermediates for the production of diphenyl ether herbicides, U.S. Pat. No. 4,329,488 (European Patent Application 30,702); synthesis and analgesic, sedative and anticonvulsant properties of m-(trifluoromethyl)benzyl methyl ketone derivatives, including [[[1-methyl-2-[3-(trifluoromethyl)phenyl]ethylidene]amino]oxy]-acetic acid, have been explored, Chem Abstracts 77:139518h; and the synthesis and resolution of dl-alpha-(isopropylideneaminooxy)propionic acid are also known, Chem Abstracts 63:5523(b) (1965).

However, none of these publications recognize the class of compounds and compositions of the present invention which have a broad spectrum of herbicidal activity and which are herbicidal toward difficult to control weeds such as cocklebur, sicklepod, velvetleaf and nutsedge.

DISCLOSURE OF THE INVENTION

In accordance with the present invention, there is provided the new class of ethylideneaminooxyacetic acids and esters of the formula (I)

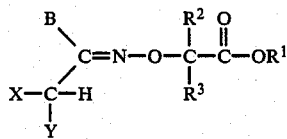

wherein
$R^1$ is hydrogen, $(C_1-C_6)$alkyl, $(C_3-C_8)$cycloalkyl, $[(C_1-C_3)$alkoxy$]_n(C_1-C_6)$alkyl, preferably a $[(C_1-C_3)$alkoxy$]_n(C_1-C_3)$alkyl, $[(C_1-C_3)$alkoxy$]_n$aryl, preferably a $[(C_1-C_3)$alkoxy$]_n$phenyl, wherein n is 0 or 1 and the aryl may be substituted with up to three, preferably up to two or more preferably up to one substituent, each independently selected from halogen, $(C_1-C_6)$alkoxy, cyano or trifluoromethyl groups; phenyl$(C_1-C_6)$alkyl, aryl or agronomically acceptable cations;
$R^2$ and $R^3$ are each independently hydrogen, optionally substituted $(C_1-C_6)$alkyl, optionally substituted $(C_3-C_8)$cycloalkyl, optionally substituted phenyl($C_1-C_2)$alkyl, wherein the substituents are up to three, preferably up to two and more preferably up to one each substituent independently selected from halogen, $(C_1-C_6)$alkoxy, cyano or trifluoromethyl, carboxy or an agronomically acceptable salt thereof, $(C_1-C_6)$alkoxycarbonyl ($-CO_2R$) and phenyl group;
X is hydrogen, fluoro, bromo, chloro or iodo atom;
Y is a hydrogen, fluoro, bromo, iodo, $(C_1-C_6)$alkyl, $(C_3-C_8)$cycloalkyl, carboxy or an agronomically acceptable salt thereof, $(C_1-C_6)$alkoxycarbonyl, phenyl$(C_1-C_6)$alkyl, $(C_2-C_6)$alkenyl and $(C_2-C_6)$alkynyl group wherein the alkyl, cycloalkyl and phenylalkyl group may have up to three, preferably up to two and more preferably up to one substituent each independently selected from halogen, trifluoromethyl, cyano or $(C_1-C_6)$alkoxy; and
B is hydrogen, carboxy or an agronomically acceptable salt thereof, carbo$(C_1-C_6)$alkoxycarbonyl, methylene ($-CH_2R^4$) or $CZZ^1Z^2$ group wherein $R^4$ is a $(C_1-C_6)$alkyl or $(C_2-C_6)$alkenyl group and Z, $Z^1$ and $Z^2$ are each independently a hydrogen, fluoro, bromo, chloro or iodo atom; provided that for any one molecule X, Y, Z, $Z^1$ and $Z^2$ are not all hydrogen atoms.

Preferred compounds of the invention are those wherein $R^1$ is hydrogen, $(C_1-C_6)$alkyl, $(C_3-C_8)$cycloalkyl, sodium, potassium, ammonium or a mono, di or tri$(C_1-C_4)$alkyl ammonium; $R^2$ and $R^3$ are each independently hydrogen, $(C_1-C_2)$alkyl or carboxy group or agronomically acceptable salts thereof, wherein the alkyl may be optionally substituted with up to one substituent selected from fluoro, chloro, bromo, iodo, $(C_1-C_2)$alkoxy, cyano or trifluoromethyl group; X is a fluoro, bromo or chloro atom; Y is a hydrogen, carboxy or an alkali metal or ammonium salt thereof or $(C_1-C_6)$alkoxycarbonyl group; and B is hydrogen or $CZZ^1Z^2$ group wherein Z, $Z^1$ and $Z^2$ are each independently a hyrogen, fluoro, bromo or chloro atom.

More preferred compounds of the invention are those wherein $R^1$ is hydrogen, $(C_1-C_2)$alkyl, sodium, potassium, ammonium or a $(C_1-C_2)$alkyl substituted ammonium; $R^2$ is hydrogen; $R^3$ is a hydrogen, methyl or ethyl group; X is a bromo or chloro atom; Y is a hydrogen, bromo, chloro, carboxy or an alkali metal or ammonium salt thereof, methoxy or ethoxy group; B is hydrogen or $CZZ^1Z^2$ wherein Z and $Z^1$ are hydrogen atoms and $Z^2$ is a bromo or chloro atom.

Alkyl group as used herein includes both straight and branched chain configurations.

The term aryl as used herein means a phenyl or naphthyl group.

By agronomically acceptable cation or salt is meant any cation or salt which can be used to form a salt with a compound of this invention without impairing the herbicidal effectiveness of the compound and which by itself has no detrimental effect on the soil, equipment, crops or agronomic environment. Further, for the purpose of this invention, when $R^1$ is a hydrogen or Y or B is a carboxy, agronomically acceptable salts and esters thereof are considered functionally equivalent. Examples of agronomically acceptable salts and cations include alkali metal, alkaline earth metal, such as sodium, potassium, lithium and magnesium, ammonium salts, including mono-, di- and tri$(C_1-C_6)$alkyl substituted ammonium, sulfonium and sulfoxonium salts such as $-S(O)_nR'$, wherein n is 0, 1 or 2 and R' is an alkyl, phenyl or NR''R''' wherein each R'' is independently a hydrogen, alkyl or phenyl, and phosphonium salts. Examples of esters include substituted and unsubstituted alkyl esters, preferably lower alkyl esters of from 1 to 6 carbon atoms, for example, methyl, ethyl, propyl, butyl, tert-butyl, pentyl and hexyl esters wherein the substituents on the lower alkyl may be selected from alkoxy, for example, lower alkoxy such as methoxy, ethoxy, propoxy and butoxy; halo-alkoxy, for example, halo lower alkoxy such as chloroethoxy and bromoethoxy; and trihalomethylalkoxy such as trifluoromethylmethoxy. Also included are alkenyl esters of from 3 to 5 carbon atoms, for example, alkyl, propynyl, alpha-methylallyl and alpha-ethylallyl.

Typical compounds included in the invention are as follows:
ethylideneaminooxy acetic acid
beta-chloroethylidene-alpha-aminooxyisobutyric acid
beta,beta'-dichloroisopropylidene-alpha-aminooxy-isobutyric acid
methyl beta-chloroethylidene-alpha-aminooxy-isobutyrate
beta-chloroethylidene-alpha-aminooxypropionic acid
beta,beta'-dichloroisopropylidene-alpha-aminooxy-propionic acid
methyl beta,beta'-dichloroisopropylidene-alpha-aminooxy-propionate
methyl beta-chloroethylidene-alpha-aminooxypropionate
beta-chloroethylideneaminooxyacetic acid
beta,beta'-dichloroisopropylideneaminooxyacetic acid
methyl beta,beta'-dichloroisopropylideneaminooxyacetate
methyl beta-chloroethylideneaminooxyacetate
ethyl beta-chloroethylideneaminooxyacetate
phenyl beta-chloroethylideneaminooxyacetate
benzyl beta-chloroethylideneaminooxyacetate
beta-bromo-gamma-carboxyisobutyleneaminooxyacetic acid
beta-chloro-gamma-carboxyisobutyleneaminooxyacetic acid
beta-chloro-gamma-carbomethoxyisobutyleneaminooxyacetic acid
beta-bromoisopropylideneaminooxyacetic acid, as well as salts of the above acids, particularly sodium, potassium, ammonium and triethyl ammonium salts.

Preferred compounds of the invention include:
beta-chloroethylidene-alpha-aminooxypropionic acid,
beta-chloroethylidene-alpha-aminooxybutyric acid,
beta,beta'-dichloroisopropylideneaminooxy acetic acid,
beta-chloro-sec-butenylideneaminooxy acetic acid,
beta-chloroisopropylideneaminooxyacetic acid,
beta-fluoroisopropylideneaminooxyacetic acid,
alpha-phenyl-alpha-chloropropenylaminooxy acetic acid,
delta-chloro-2-butenylideneaminooxyacetic acid,
alpha-(4-bromophenyl)-beta-bromoethylideneaminooxy acetic acid,
beta-chloro-beta'-carboethoxy isopropylideneaminooxy acetic acid,
beta-chloro-beta-carboethoxyisopropylideneaminooxyacetic acid,
methyl beta-chloroethylideneaminooxyacetate,
ethyl beta-chloroethylideneaminooxyacetate and
propyl beta-chloroethylideneaminooxyacetate and the sodium, potassium, ammonium and triethyl ammonium salts of the above acids.

More preferred compounds include:
beta-bromoethylidene-alpha-aminooxypropionic acid
beta-chloroethylideneaminooxyacetic acid
beta-bromoethylideneaminooxyacetic acid
beta-chloroisopropylideneaminooxyacetic acid
beta-bromoisopropylideneaminooxyacetic acid
beta,beta'-dichloroisopropylideneaminooxyacetic acid
beta,beta'-dibromoisopropylideneaminooxyacetic acid
delta-chloro-2-butenylideneaminooxyacetic acid
methyl beta-chloroethylideneaminooxyacetate and the sodium, potassium, ammonium and triethyl ammonium salts of the above acids.

Compounds of this invention can be prepared by utilizing conventional techniques. For example, by the condensation of aminooxyacetic acid, e.g., as its hydrochloride or hemihydrochloride salt, with the appropriate ketone or aldehyde in the presence of an acid or a base at a temperature of from about −30° to about 100° C., preferably from about 10° to about 50° C. Suitable solvents include dimethylformamide (DMF), tetrahydrofuran (THF), dimethoxyethane and dioxane which are mixed with about 10–20 percent by volume water. Suitable acids include hydrochloric, p-toluenesulfonic, sulfuric and acetic and suitable bases include alkali metal, for example, sodium and potassium, hydroxides, carbonates, and bicarbonates and tertiary amines such as triethylamine. Such a process (II) is illustrated below:

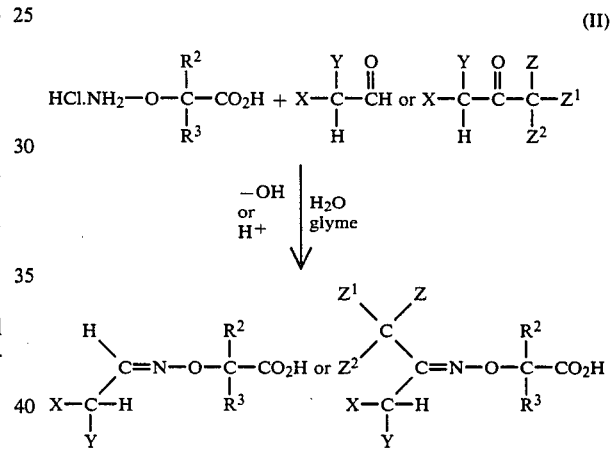

Alternatively, oxime derivatives may be condensed in the presence of base, such as an alkali metal carbonate, e.g., sodium or potassium carbonate or a tertiary amine, e.g., triethylamine, with the appropriate halogenated acetic acid derivatives at a temperature of preferably from about 0° to 100° C., more preferably about 50° C., as shown in reaction scheme (III) below. Suitable solvents include DMF, THF and dimethoxyethane mixed with water. Thereafter, an acid such as acetic, hydrochloric or sulfuric acid in water is added to obtain the desired ethylideneaminooxyacetic acid.

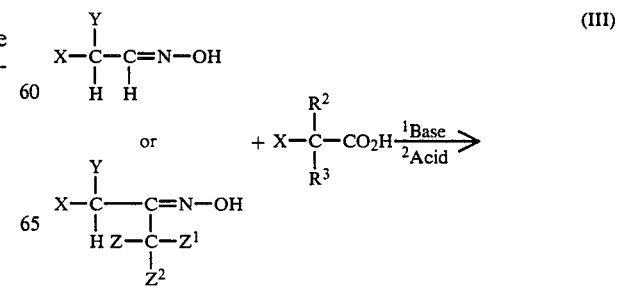

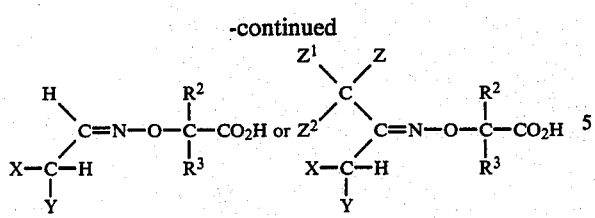

The corresponding esters and salts of the acids can be obtained by classical techniques. The esters, for example, by using thionyl chloride or chloroformates in an excess of the appropriate alcohol. Salts of the acids can be obtained by conventional techniques such as by titration with the appropriate salt in water or with the appropriate amine.

The novel compounds of the invention are useful both as preemergent and as postemergent herbicides, preferably as preemergent herbicides. Preemergence herbicides are ordinarily used to treat the soil in which the desired crop is to be planted by application either before seeding, during seeding, or, as in most applications, after seeding and before the crop emerges. Postemergence herbicides are those which are applied after the weed plants have emerged and during their growth period. Among the crops on which the compounds of the invention can be advantageously employed are, for example, corn, wheat, and oats.

When used as herbicides the invention further includes compounds of formula I wherein Y can additionally be a phenyl group optionally substituted with up to three, preferably up to two and more preferably up to one substituent independently selected from halogen, trifluoromethyl, $(C_1-C_6)$alkoxy, preferably a $(C_1-C_2)$alkoxy, nitro, $C_1-C_6$alkoxycarbonyl, preferably a $(C_1-C_2)$alkoxycarbonyl, $(C_1-C_6)$alkyl, preferably a $(C_1-C_2)$alkyl, and aryl, preferably a phenyl group. These compounds can be prepared by utilizing conventional techniques as described previously herein.

The ethylideneaminooxyacetic acids and esters of this invention can be applied in any amount which will give the required control of weeds. Generally, the rate of application of the herbicides of the invention will be from about 0.2 to about 10, preferably from about 0.5 to about 5 and more preferably from about 1 to about 3 kilograms (kg) per hectare (ha).

Under some conditions, the compounds of the invention may be advantageously incorporated into the soil or other growth medium prior to planting a crop. This incorporation can be carried out by any convenient means, including by simple mixing with the soil, by applying the compounds to the surface of the soil and then disking or dragging into the soil to the desired depth, or by employing a liquid carrier to accomplish the necessary penetration and impregnation.

When used in transplanted rice crops, the compounds of the invention can be applied either preemergence or postemergence to the weeds—that is, they can be applied to the growth medium of the transplanted plants either before the weed plants have emerged or while they are in their early stages of growth. The compounds can be applied to the growth medium either before or after the rice has been transplanted to that medium.

A compound of the invention can be applied to the growth medium or to plants to be treated either by itself or, as is generally done, as a component in a herbicidal composition or formulation which also comprises an agronomically acceptable carrier. By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the compounds of the invention may also be used in any of these herbicidal formulations. The herbicidal compositions of the invention can be either solid or liquid formulations or solutions. For example, the compounds of the invention can be formulated as solutions, wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The compounds of this invention can be dissolved in any appropriate solvent. Examples of solvents which are useful in the practice of this invention include water, alcohols, ketones, halogenated hydrocarbons, dimethylformamide, dioxane, dimethyl sulfoxide, and the like. Mixtures of these solvents can also be used. The concentration of the solution can vary from about 2% to about 98% with a preferred range being about 25% to about 75%.

For the preparation of emulsifiable concentrates, the compounds can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols of long-chain alcohols, mercaptans, carboxylic acids, and reactive amines and partially esterified polyhydric alcohols. Solvent-soluble sulfates or sulfonates, such as the alkaline earth salts or ammonium salts of sulfates and sulfonates, alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent, such as a water-soluble cellulose derivative or a water-soluble salt of a polyacrylic acid. The concentration of the active ingredient in emulsifiable concentrates is usually about 10% to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid, such as granular fuller's earth, vermiculite, ground corn cobs, seed hulls, including bran or other grain-hulls, or similar material. A solution of one or more of the compounds in a volatile organic solvent can be sprayed or mixed with the granular solid and the solvent then removed by evaporation. The granular material can have any suitable size, with a preferable size range of 16 to 60 mesh. The compounds will usually comprise about 2 to 15% of the granular formulation.

The compounds of the invention can be applied as herbicidal sprays by methods commonly employed, such as conventional high-gallonage hydraulic sprays, low gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with the compounds of the invention. Examples of other herbicides which can be incorporated to provide additional advantages and effectiveness include:

CARBOXYLIC ACIDS AND DERIVATIVES 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and its salts and esters
2,3,6-trichlorophenylacetic acid and its salts
3,7-endoxohexahydrophthalic acid
Dimethyl 2,3,5,6-tetrachloroterephthalate
Trichloroacetic acid and its salts
2,2-dichloropropionic acid and its salts
2,3-dichloroisobutyric acid and its salts

CARBAMIC ACID DERIVATIVES

Ethyl N,N-di(n-propyl)thiolcarbamate
Propyl N,N-di(n-propyl)thiolcarbamate
Ethyl N-ethyl-N-(n-butyl)thiolcarbamate
Propyl N-ethyl-N-(n-butyl)thiolcarbamate
2-chloroallyl N,N-diethyldithiocarbamate
N-methyldithiocarbamic acid salts
Ethyl 1-hexamethyleneiminebarbothiolate
Isopropyl N-phenylcarbamate
Isopropyl N-(m-chlorophenyl)carbamate
4-chloro-2-butynyl N-(m-chlorophenyl)carbamate
Methyl N-(3,4-dichlorophenyl)carbamate

PHENOLS

Dinitro-o-(sec-butyl)phenol and its salts
Pentachlorophenol and its salts

SUBSTITUTED UREAS 3-(3,4-dichlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-2-n-butyl-1-methylurea
3-(3,4-dichlorophenyl)-1-methoxy-1-methylurea
3-(4-chlorophenyl-1-methoxy-1-methylurea
3-(3,4-dichlorophenyl)-1,1,3-trimethylurea
3-(3,4-dichlorophenyl)-1,1-diethylurea
Dichloral urea

SUBSTITUTED TRIAZINES 2-chloro-4,6-bis(ethylamino)-2-triazine
2-chloro-4-ethylamino-6-isopropylamino-s-triazine
2-chloro-4,6-bis(methoxypropylamino)-2-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2-methoxy-4-ethylamino-6-isopropylamino-s-triazine
2-methylmercapto-4-(2-methoxyethylamino)-6-isopropylamino-s-triazine

DIPHENYL ETHER DERIVATIVES 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether
2,4-dichloro-3'-methoxy-4'-nitrodiphenyl ether
2-chloro-4-trifluoromethyl-3'-[2-(methoxycarbonyl)ethoxycarbonyl]-4'-nitro diphenyl ether
2-chloro-4-trifluoromethyl-3'-[1-(methoxycarbonyl)ethoxycarbonyl]-4'-nitrodiphenyl ether
2-chloro-4-trifluoromethyl-3'-[(ethoxycarbonyl)methoxycarbonyl]-4'-nitrodiphenyl ether
5-(2-chloro-4-trifluoromethylphenoxy)-2-nitro-N-methanesulfonyl benzamide
Sodium 5-(2-chloro-4-(trifluoromethyl)phenoxy)-2-nitrobenzoate
2-chloro-1-(3-ethoxy-4-nitrophenoxy)-4-(trifluoromethyl)benzene
Ethyl 5-(2-chloro-4-(trifluoromethyl)phenoxy)-2-nitrobenzoate
Methyl 5-(2-chloro-4-(trifluoromethyl)phenoxy)-2-nitrobenzoate
2-chloro-4-trifluoromethyl-3'-[1-(ethoxycarbonyl)ethoxycarbonyl]-4'-nitrodiphenyl ether

ANILIDES

N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-alpha,alpha-dimethylveramide
N-isopropyl-N-phenylchloroacetamide
N-n-butoxymethyl-N-(2,6-diethylphenyl)chloroacetamide
N-n-methoxymethyl-N-(2,6-diethylphenyl)chloroacetamide

URACILS 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil

NITRILES 2,6-dichlorobenzonitrile
Diphenylacetonitrile
3,5-dibromo-4-hydroxybenzonitrile
3,5-diiodo-4-hydroxybenzonitrile

OTHER ORGANIC HERBICIDES 2-chloro-N,N-diallylacetamide
N-(1,1-dimethyl-2-propynyl)-3,5-dichlorobenzamide
maleic hydrazide
3-amino-1,3,4-triazole monosodium methanearsonate disodium methanearsonate
N,N-dimethyl-alpha,alpha-diphenylacetamide
N,N-di(n-propyl)-2,6-dinitro-4-trifluoromethylaniline
N,N-di(n-propyl)-2,6-dinitro-4-methylaniline
N,N-di(n-propyl)-2,6-dinitro-4-methylsulfonylaniline
O-(2,4-dichlorophenyl)-O-methyl-isopropylphosphoramido-thioate
4-amino-3,5,6-trichloropicolinic acid
2,3-dichloro-1,4-naphthoquinone-di(methoxythiocarbonyl)disulfide
3-isopropyl-1H-2,1,3-benzothiadiazine-(4)3H-one-2,2-dioxide
6,7-dihydrodipyrido[1,2-a:2',1'-c]pyrazidinium salts
1,1'-dimethyl-4,4'-bipyridinium salts
3,4,5,6-tetrahydro-3,5-dimethyl-2-thio-2H-1,3,5-thiadiazine
2-chloro-N-[(4-methoxy-6-methyl-1,3,5-triazin-2-yl)amino carbonyl]benzene sulfonamide
2-(1-allyloxyamino-butylidine)-4-carbomethoxy-5-dimethyl-cyclohexan-1,3-dione
2,(1-ethoxyamino-butylidine)-5-(2-ethylsulfinylpropyl)-cyclohexan-1,3-dione
Butyl-2-[4-(5-trifluoromethyl-2-pyridyloxy)phenoxy]-propionate.

When mixtures of herbicides are employed, the relative proportions which are used will depend upon the crop to be treated and the degree of selectivity in weed control which is desired.

EXAMPLES

The following compounds summarized in Table 1 are meant to be illustrative of the invention.

TABLE 1

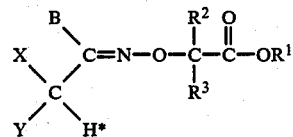

| Cpd | B | X | Y | $R^1$ | $R^2$ | $R^3$ | Elemental Analysis Calculated (Found) |
|---|---|---|---|---|---|---|---|
| 1 | H | H | H | H | H | H | C: 41(40.77) H: 6(5.93) N: 12(11.95) |
| 2 | H | H | Et | H | H | H | C: 45.8(46.08) H: 6.9(7.02) N: 10.7(9.31) |
| 3 | H | =CH$_2$ | CH$_3$ | H | H | H | C: 50.0(50.11) H: 6.9(6.63) N: 9.7(9.43) |
| 4 | H | H | i-propyl | H | H | H | C: 52.8(52.60) H: 8.2(8.16) N: 8.8(8.54) |
| 5 | H | H | CH=C—CH$_3$ | H | H | H | C: 50.3(50.34) H: 6.3(6.52) N: 9.8(9.68) |
| 6 | CH$_3$ | Cl | CO$_2$Et | H | H | H | C: 40.4(40.30) H: 5.1(4.98) N: 5.9(5.97) |
| 7 | CF$_3$ | Br | H | H | H | H | C: 22.7(24.23) H: 1.9(2.13) N: 5.3(5.60) Br: 30.3(30.61) F: 21.6(21.92) |
| 8 | H | Cl | H | H | CH$_3$ | H | C: 36.2(35.42) H: 4.8(4.84) N: 8.5(7.90) |
| 9 | H | H | H | H | CH$_3$ | H | C: 45.8(44.26) H: 6.9(7.09) N: 10.7(10.29) |
| 10 | CH$_3$ | H | H | H | CH$_3$ | H | C: 49.6(49.95) H: 7.6(7.59) |

TABLE 1-continued $$\begin{array}{c} B \\ X \diagdown \\ \diagdown C=N-O-\overset{R^2}{\underset{R^3}{C}}-\overset{O}{\underset{}{C}}-OR^1 \\ Y \diagup \overset{|}{C} \diagdown \\ H^* \end{array}$$

| Cpd | B | X | Y | R¹ | R² | R³ | Elemental Analysis Calculated (Found) |
|---|---|---|---|---|---|---|---|
| 11 | CH₃ | H | OCH₃ | H | H | H | N: 9.7(9.26)<br>C: 44.72(44.38)<br>H: 6.8(7.35) |
| 12 | CH₃ | Cl | Cl | H | H | H | N: 8.7(8.14)<br>C: 30.0(30.16)<br>H: 3.5(3.50) |
| 13 | H | I | H | H | H | H | N: 7.0(6.98)<br>NMR (CDCl₃): 3.8 ppm (doublet, J = 7 Hz); 3.9 ppm (doublet, J = 7 Hz); 4.6 ppm (singlet); 7.0 ppm (triplet, J = 6 Hz); 7.6 ppm (triplet, J — 6 Hz) |
| 14 | CH₂Br | Br | H | H | H | H | C: 20.8(24.18)<br>H: 2.4(2.95)<br>N: 4.8(5.63)<br>Br: 55.4(59.41) |
| 15 | CH₃ | F | H | H | H | H | C: 40.2(40.39)<br>H: 5.4(5.60)<br>N: 9.4(9.51) |
| 16 | CH₂Cl | H | H | H | H | H | C: 36.2(36.03)<br>H: 4.8(4.97)<br>N: 8.5(8.13) |
| 17 | CH₂Cl | Cl | H | H | H | H | C: 30.0(30.03)<br>H: 3.5(3.49)<br>N: 7.0(6.89) |
| 18 | CHBrCH₃ | Br | CH₃ | H | H | H | C: 26.5(30.35)<br>H: 3.5(4.10)<br>N: 4.4(5.25) |
| 19 | CH₂Cl | H | C(O)OCH₃ | H | H | H | C: 37.6(37.13)<br>H: 4.5(4.57)<br>N: 6.3(6.23) |
| 20 | CH₃ | Cl | C(O)OCH₃ | H | H | H | C: 37.6(37.68)<br>H: 4.5(4.59)<br>N: 6.3(6.5) |
| 21 | CH₂Cl | H | C(O)OEt | H | H | H | C: 40.4(40.04)<br>H: 5.1(4.97)<br>N: 5.9(5.95) |
| 22 | CH₃ | Cl | CH₃ | H | H | H | C: 40.1(40.23)<br>H: 5.6(5.52)<br>N: 7.8(7.72) |
| 23 | C(O)OH | Br | H | H | H | H | C: 25(26.91)<br>H: 2.5(2.70)<br>N: 5.8(6.20) |
| 24 | CH₂Br | H | CH₃ | H | H | H | C: 32.1(36.59)<br>H: 4.5(5.0)<br>N: 6.2(7.08) |
| 25 | H | Cl | Cl | H | H | H | C: 25.8(25.61)<br>H: 2.7(2.8)<br>N: 7.5(7.01) |
| 26 | H | Br | H | H | H | H | C: 24.5(25.02)<br>H: 3.1(3.26)<br>N: 7.1(7.02) |
| 27 | CH₃ | Br | H | H | H | H | C: 28.6(29.43)<br>H: 3.8(3.88)<br>N: 6.7(6.81) |
| 28 | H | H | H | H | Et | H | C: 49.6(49.86)<br>H: 7.6(7.71)<br>N: 9.7(9.49) |
| 29 | H | H | =C(CH₂)₂CH₃ | H | H | H | C: 56.1(55.92)<br>H: 7.6(7.65)<br>N: 8.2(8.03) |
| 30 | CH₂Br | H | C(O)OEt | H | H | H | C: 31.3(34.75)<br>H: 3.7(4.08)<br>N: 5.2(5.94) |
| 31 | H | Br | H | H | CH₃ | H | C: 28.6(29.63)<br>H: 3.8(3.98)<br>N: 6.7(6.8) |
| 32 | CH₃ | Br | CH₃ | H | H | H | C: 32.1(31.84)<br>H: 4.5(4.11) |

TABLE 1-continued $$\begin{array}{c} B \\ X \\ \diagdown \\ C \\ \diagup \\ Y \end{array} C=N-O-\underset{\underset{R^3}{|}}{\overset{\overset{R^2}{|}}{C}}-\overset{\overset{O}{\|}}{C}-OR^1$$

| Cpd | B | X | Y | R¹ | R² | R³ | Elemental Analysis Calculated (Found) |
|---|---|---|---|---|---|---|---|
| 33 | H | Cl | H | CH₃ | H | H | N: 6.2(5.94)<br>C: 36.2(36.37)<br>H: 4.8(4.87) |
| 34 | H | Cl | H | Et | H | H | N: 8.46(8.39)<br>C: 40.1(40.62)<br>H: 5.6(5.74) |
| 35 | H | Cl | H | n-propyl | H | H | N: 7.8(7.96)<br>C: 43.4(44.08)<br>H: 6.2(6.52) |
| 36 | H | Cl | H | i-propyl | H | H | N: 7.2(7.24)<br>C: 43.4(43.71)<br>H: 6.2(6.35) |
| 37 | H | Cl | H | n-butyl | H | H | N: 7.2(7.43)<br>C: 46.3(48.02)<br>H: 6.75(7.37) |
| 38 | H | Cl | H | n-pentyl | H | H | N: 6.75(6.34)<br>C: 48.8(49.64)<br>H: 7.2(7.57) |
| 39 | C(O)OH | F | H | H | H | H | N: 6.3(6.23)<br>C: 33.5(33.47)<br>H: 3.4(3.42) |
| 40 | CH₃ | H | —CH₂CH₂Cl | H | H | H | N: 7.8(7.79)<br>C: 43.4(46.21)<br>H: 6.2(6.79) |
| 41 | H | Cl | H | H | H | H | N: 7.2(7.27)<br>C: 31.6(31.86)<br>H: 3.9(3.93)<br>N: 9.2(9.18)<br>Cl: 23.3(23.51) |
| 42 | H | Cl | H | CH₃ | CH₃ | H | C: 40.4(40.57)<br>H: 5.0(5.28)<br>N: 5.9(6.20)<br>Cl: 14.9(14.97) |
| 43 | H | Cl | H | n-butyl | H | H | C: 47.7(47.91)<br>H: 7.1(7.38)<br>N: 5.6(6.53)<br>Cl: 14.1(14.21) |
| 44 | H | Cl | H | —(CH₂)₂OCH₃ | H | H | C: 40.1(39.79)<br>H: 5.7(5.99)<br>N: 6.7(7.17)<br>Cl: 16.9(17.4) |

*In Examples 3 and 29, this hydrogen does not exist.

EXAMPLE 1

Ethylideneaminooxyacetic acid

A 100 ml single necked round bottomed flask was equipped with a stirring bar and reflux condenser. The flask was charged with aminooxyacetic acid hemihydrochloride (3.0 gm, 14 mmoles) and 15 ml deionized water. Acetaldehyde (1.25 gm, 28 mmoles) was added in one portion. This mixture was adjusted to pH 8-9 by the addition of 20% aqueous sodium hydroxide. The resulting solution was then heated on a steam bath for about 1.5 hours, the solution was cooled to ambient temperature, then extracted with diethyl ether. The ether extracts were discarded. The aqueous phase was acidified (pH 4-5) with concentrated hydrochloric acid, then extracted with diethylether (3×25 ml). The combined extracts were dried over magnesium sulfate. The solvent was removed in vacuo to leave a yellow oil. Vacuum distillation gave the desired product (1.6 gm) as a yellow oil (b.p. 120°-125° C., 0.9 mm Hg).

EXAMPLE 13

Beta-Iodoethylideneaminooxyacetate

A small round bottomed flask was equipped with a magnetic stirring bar. Beta-chloroethylideneaminooxyacetic acid (2.0 gm, 13 mmoles) (its preparation is described in example 41) was added to the flask along with dimethyl sulfoxide (10 ml). Potassium iodide (5.0 gm, 30 mmoles) was added and the resulting mixture stirred at room temperature for one hour. Diethyl ether (about 20 ml) and cold water (about 5 ml) were added. The layers were separated. The ether phase was washed with water then dried over magnesium sulfate. The solvent was removed in vacuo to leave a dark reddish brown oil, estimated by NMR to be 75% of the desired compound.

EXAMPLE 16

Beta-Chloroisopropylideneaminooxyacetate

A 250 ml round bottomed single necked flask was equipped with a reflux condenser and stirring bar. Aminooxyacetic acid hemihydrochloride (3 gm, 14 mmoles)

was charged into the flask along with water (deionized, 10 ml). Chloroacetone (2.8 gm, 28 mmole) was dissovled in about 5 ml of glyme. This solution was added in one portion to the reaction flask. The resulting mixture was adjusted to pH 8-9 with 20% aqueous sodium hydroxide. This was warmed on a steam bath for about 2 hours, cooled to room temperature, then extracted with diethyl ether. The aqueous phase was acidified with concentrated hydrochloric acid (to pH 2-3). This was extracted with diethylether (3×25 ml). The combined extracts were dried over magnesium sulfate, then the solvent was removed in vacuo to leave a desired compound (2.8 gm) as a brown oil.

EXAMPLE 17

Beta,Beta'-Dichloroisopropylideneaminooxyacetic acid

A 100 ml single necked round bottomed flask was equipped with a magnetic stirring bar. This was charged with aminooxyacetic acid hemihydrochloride (3.0 gm, 14 mmoles). Deionized water (10 ml) and glyme (10 ml) were added. This mixture was stirred until a homogeneous solution was obtained. 1,3-dichloroacetone (3.6 gm, 28 mmoles) in 10 ml glyme was added dropwise, rapidly. After addition was complete, the resulting mixture was heated on a steam bath for about 1.5 hours. The resulting mixture was stripped in vacuo. The residual solid was shaken with dichloromethane and water. The organic layer was dried over magnesium sulfate, then filtered and stripped. There was obtained 3.9 gm of the desired compound as a light yellow solid having a melting point of 76°-78° C.

EXAMPLE 21

Beta-Chloro-beta'-carboethoxyisopropylideneaminooxyacetic acid

The procedure of example 17 was used. Aminooxyacetic acid hemihydrochloride (3.0 gm, 14 mmoles) and ethyl 4-chloroacetoacetate (4.5 gm, 28 mmoles) were combined in water and heated for 2 hours on a steam bath. The resulting mixture was cooled and extracted with diethyl ether. The combined ether layers were dried over magnesium sulfate, then taken to "dryness" in vacuo. There was obtained 2.8 gm of the desired product as a yellow oil.

EXAMPLE 26

Beta-Bromoethylideneaminooxyacetic acid

A 250 ml round bottomed single necked flask was equipped with a stirring bar. Aminooxyacetic acid hemihydrochloride (3.0 gm, 14 mmoles) was placed into the flask along with deionized water (10 ml). The resulting solution was cooled to 5°-10° C. Bromoacetal (5.3 gm, 28 mmoles) was added to this reaction mixture. Concentrated hydrochloric acid (50 ml) was added dropwise while stirring vigorously. A homogeneous solution was obtained. This was extracted with diethyl ether (4×10 ml) and the combined extracts were dried over magnesium sulfate. The solvent was stripped in vacuo to leave the desired product (2.3 gm) as a brown solid having a melting point of 56°-58° C.

EXAMPLE 31

Beta-Bromoethylidene-alpha-aminooxypropionic acid (a) N-Hydroxymethyl urethane

A one liter, three necked round bottomed flask was equipped with two addition funnels and a paddle stirrer. The flask was charged with hydroxylamine hydrochloride (35 gm, 0.5 mole) in water (100 ml). One addition funnel was filled with 50% aqueous sodium hydroxide (80 gm, 1 mole). The other addition funnel was filled with methyl chloroformate (48 gm, 0.5 mole). The reaction mixture was cooled to 10°-15° C. during the concurrent addition of sodium hydroxide and methyl chloroformate. This required approximately one hour. The resulting mixture was acidified with concentrated hydrochloric acid (to pH 3-4), then extracted with ethyl acetate. The organic extract was dried over magnesium sulfate, then the solvent was removed in vacuo to leave the desired N-hydroxymethyl urethane (17.0 gm), as a clear oil which was solidified on standing.

(b) N-Carbomethoxy-alpha-aminooxypropionic acid hydrochloride

A 500 ml single necked round bottomed flask was equipped with a stirring bar. The flask was charged with 2-bromopropionic acid (28.6 gm, 0.187 mole), water (100 ml) and sodium hydroxide (14.9 gm, 50% aqueous 0.187 mole). N-hydroxymethyl urethane (17.0 gm, 0.187 mole) was added in one portion, followed by another equivalent of 50% aqueous sodium hydroxide (14.9 gm). The resulting solution was warmed on a steam bath for about 4 hours. This solution was cooled to room temperature and adjusted to pH 4 with concentrated hydrochloric acid. The resulting mixture was extracted with ethyl acetate. The organic extracts were dried over magnesium sulfate then taken to residue in vacuo to leave N-carbomethoxy-alpha-aminooxypropionic acid as a clear oil. This was crystallized from diethyl ether to give 15.1 gm of the compound as a white solid having a melting point of 85°-92° C. This compound was stirred with concentrated hydrochloric acid (30 ml) in a 50 ml Erlenmeyer flask for about five hours. Water and acid were removed in vacuo to leave N-carbomethoxy-alpha-aminooxypropionic acid hydrochloride (6.9 gm) having a melting point of 144°-48° C.

(c) Beta-Bromoethylidene-alpha-aminooxypropionic acid

A 250 ml round bottomed single necked flask was equipped with a magnetic stirring bar. The flask was charged with racemic N-carbomethoxy-alpha-aminooxypropionic acid hydrochloride (6.9 gm, 0.048 mole). Water was then added (20 ml), followed by bromoacetal (9.5 gm, 0.048 mole). This mixture was cooled to about 5° C. in an ice bath. Cold, concentrated hydrochloric acid (100 ml) was added. The resulting mixture was stirred at ice-water bath temperature for about one hour, then allowed to stir at room temperature for an additional two hours. This solution was concentrated in vacuo. The residue obtained was dissolved in diethyl ether. The ether layer was washed with aqueous 5% sodium bicarbonate solution. The aqueous phase was made acidic with concentrated hydrochloric acid, then extracted with dichloromethane (4×20 ml). The combined extracts were dried over magnesium sulfate and concentrated in vacuo to obtain the desired beta-bromoethylidene-alpha-aminooxypropionic acid (2.8 gm) as a solid having a melting point of 53°-55° C.

EXAMPLE 34

Ethyl beta-chloroethylideneaminooxyacetate

A dry 25 ml two-necked round bottom flask was equipped with a stirring bar, addition funnel, reflux condenser and nitrogen bubbler. The flask was charged with absolute ethanol (9.2 gm, 200 mmoles) and the addition funnel charged with thionyl chloride (4.3 gm, 36 mmoles). The flask and its contents were cooled to about 0° C. The thionyl chloride was added dropwise while maintaining the flask temperature at 5° C. or below. After the addition was completed, the resulting mixture was stirred for 1 hour at 0° C. Beta-chloroethylideneaminooxyacetic acid (2.7 gm, 18 mmoles) was added in one portion. The resulting mixture was allowed to warm to room temperature during 1 hour. The flask was warmed to 40°-45° C. and maintained for 4 hours. The resulting mixture was cooled, then solvents were removed in vacuo. The residue was taken up in ethyl acetate which was extracted with an aqueous solution of sodium bicarbonate. The ethyl acetate layer was dried over magnesium sulfate, filtered, then taken to "dryness" in vacuo. A brown oil (2.1 gm) was obtained. Distillation at 0.5 mm Hg gave the desired product as a clear oil (2.0 gm), b.p. 60°-70° C.

EXAMPLE 41

Beta-Chloroethylideneaminooxyacetic acid

A 100 ml single necked round bottomed flask was equipped with a magnetic stirring bar. This flask was charged with aminooxyacetic acid hemihydrochloride (3.0 gm, 14 mmoles) dissolved in 20 ml of deionized water. Chloroacetaldehyde (45% w/v in water, 419 gm, 28 mmoles) was added rapidly, dropwise, with stirring. A mild exotherm was noticed. The resulting mixture was heated on a steam bath for 2 hours. This solution was cooled to room temperature, then three times extracted with dichloromethane. The combined organic layers were dried over magnesium sulfate, then taken to dryness in vacuo. The desired material was obtained as a white solid, 1.7 gm having a melting point of 66°-68° C.

The remainder of the compounds were prepared in a manner analogous to the above examples.

EXAMPLE 45

Using the procedure described below, the compounds of the invention were evaluated for control of the following weeds:

Monocots
  barnyardgrass (*Echinochloa crusgalli*)
  downy brome (*Bromus tectorum*)
  foxtail (*Setaria faberii*)
  Johnsongrass (*Sorghum halepense*)
  nutsedge (*Cyperus esculentus*)
  wild oat (*Avena fatua*)
Dicots
  cocklebur (*Xanthium pensylvanicum*)
  marigold (Tagetes spp.)
  morningglory (*Ipomoea purpurea*)
  sicklepod (*Cassia obtusifolia*)
  tomato (*Lycopersicon esculentum*)
  velvetleaf (*Abutilon theophrasti*)

The following test procedure was employed. Seeds of selected crops and weeds were planted in soil in flats. For preemergence tests, the flats were treated with the test compound immediately after the planting. For postemergence tests, the seeds were allowed to germinate, and after about two weeks the flats were treated with the test compound. The compounds to be evaluated were dissolved in a 50:50 mixture of acetone and methanol containing a small amount (about 0.5 to about 1 (w/v)%) of surfactant and then diluted with acetone and sprayed over the flats using a carrier volume equivalent to 50 gallons per acre at the rate indicated in Table 2. About two weeks after the application of the test compound, the state of growth of the plants was observed and the phytotoxic effect of the compound was evaluated. Table 2 gives the average percent control against the aforementioned monocots (AM) and dicots (AD) achieved by the test compounds, 0 indicates no control (the plants looked the same as the untreated control plants) and 100 means 100% control (complete kill).

TABLE 2

| Compound | Preemergence (8 lb./Acre) | | Postemergence (4 lb./Acre) | |
|---|---|---|---|---|
| | AD | AM | AD | AM |
| 1 | 66 | 37 | 94 | 68 |
| 2 | 0 | 5 | 33 | 11 |
| 3 | 58 | 47 | 42 | 18 |
| 4 | 0 | 13 | 20 | 0 |
| 5 | 8 | 25 | 11 | 3 |
| 6 | 15 | 10 | 32 | 15 |
| 7 | 0 | 0 | 25 | 13 |
| 8 | 52 | 58 | 79 | 39 |
| 9 | 83 | 76 | 78 | 70 |
| 10 | 33 | 50 | 63 | 33 |
| 11 | 3 | 14 | 26 | 21 |
| 12 | 55 | 42 | 24 | 5 |
| 13 | 3 | 2 | 64 | 34 |
| 14 | 0 | 0 | 76 | 61 |
| 15 | 55 | 56 | 30 | 8 |
| 16 | 84 | 60 | 93 | 29 |
| 17 | 84 | 59 | 88 | 35 |
| 18 | 0 | 0 | 40 | 34 |
| 19 | 0 | 0 | 59 | 34 |
| 20 | 29 | 41 | 23 | 20 |
| 21 | 3 | 0 | 21 | 72 |
| 22 | 77 | 54 | 73 | 24 |
| 23 | 0 | 0 | 45 | 23 |
| 24 | 36 | 18 | 43 | 50 |
| 25 | 16 | 8 | 31 | 18 |
| 26 | 6 | 26 | 100 | 59 |
| 27 | 28 | 3 | 50 | 36 |
| 28 | 5 | 43 | 40 | 36 |
| 29 | 0 | 6 | 19 | 27 |
| 30 | 0 | 0 | 1 | 10 |
| 31 | 6 | 3 | 94 | 29 |
| 32 | 7 | 11 | 55 | 21 |
| 33 | 38 | 54 | 18 | 2 |
| 34 | 56 | 50 | 36 | 2 |
| 35 | 32 | 55 | 21 | 20 |
| 36 | 8 | 4 | 26 | 10 |
| 37 | 8 | 7 | 26 | 24 |
| 38 | 8 | 4 | 31 | 13 |
| 39 | 0 | 0 | 8 | 0 |
| 40 | 0 | 7 | 1 | 3 |
| 41 | 100 | 75 | 86 | 36 |
| 42 | 38* | 21* | 36 | 21 |
| 43 | 30* | 55* | 81 | 59 |
| 44 | 6* | 13* | 62 | 30 |

*4 lb./Acre.

What is claimed is:
1. A compound of the formula

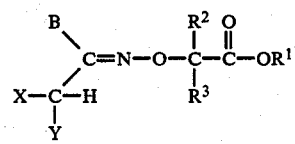

wherein
$R^1$ is hydrogen; $(C_1-C_6)$alkyl; $(C_3-C_8)$cycloalkyl; $((C_1-C_3)\text{alkoxy})_n(C_1-C_6)$alkyl, $((C_1-C_3)\text{alkoxy})_n$aryl, wherein n is 0 or 1 and the aryl may be substituted with up to three substituents each independently selected from halogen, $(C_1-C_6)$alkoxy, cyano and trifluoromethyl groups; phenyl($C_1$-$C_6$)alkyl; aryl; or agronomically acceptable cations;

$R^2$ and $R^3$ are each independently hydrogen; optionally substituted ($C_1$-$C_6$)alkyl, optionally substituted ($C_3$-$C_8$)cycloalkyl, optionally substituted phenyl($C_1$-$C_2$)alkyl, wherein the substituents are up to three substituents each independently selected from halogen, ($C_1$-$C_6$)alkoxy, cyano or trifluoromethyl; carboxy or an agronomically acceptable salt thereof, ($C_1$-$C_6$)alkoxycarbonyl or phenyl group;

X is a hydrogen, fluoro, bromo, chloro or iodo atom;

Y is a hydrogen, fluoro, bromo, iodo, ($C_1$-$C_6$)alkyl, ($C_3$-$C_8$)cycloalkyl, carboxy, or agronomically acceptable salts thereof, ($C_1$-$C_6$)alkoxycarbonyl, phenyl($C_1$-$C_6$)alkyl, ($C_2$-$C_6$)alkenyl and ($C_2$-$C_6$)alkynyl group wherein the alkyl, cycloalkyl, phenylalkyl and phenyl group may have up to three substituents each independently selected from the group consisting of halogen, trifluoromethyl, cyano and ($C_1$-$C_6$)alkoxy groups; and B is hydrogen, carboxy or an agronomically acceptable salt thereof, ($C_1$-$C_6$)alkoxycarbonyl, methylene (=$CH_2R^4$) or $CZZ^1Z^2$ group wherein $R^4$ is a ($C_2$-$C_6$)alkenyl group and Z, $Z^1$ and $Z^2$ are each independently a hydrogen, fluoro, bromo, chloro or iodo atom; provided that for any one molecule X, Y, Z, $Z^1$ and $Z^2$ are not all hydrogen atoms.

2. A compound of the formula $$\begin{array}{c} B \\ \diagdown \\ C=N-O-C-C-OR^1 \\ \diagup \quad\quad | \quad || \\ X-C-H \quad R^2 \; O \\ | \quad\quad\quad\quad R^3 \\ Y \end{array}$$

wherein $R^1$ is hydrogen; ($C_1$-$C_6$)alkyl; ($C_3$-$C_8$)cycloalkyl; (($C_1$-$C_3$)alkoxy)$_n$($C_1$-$C_6$)alkyl, (($C_1$-$C_3$)alkoxy)$_n$aryl, wherein n is 0 or 1 and the aryl may be substituted with up to three substituents each independently selected from halogen, ($C_1$-$C_6$)alkoxy, cyano and trifluoromethyl groups; phenyl($C_1$-$C_6$)alkyl; aryl; or agronomically acceptable cations;

$R^2$ and $R^3$ are each independently hydrogen; optionally substituted ($C_1$-$C_6$)alkyl, optionally substituted ($C_3$-$C_8$)cycloalkyl, optionally substituted phenyl($C_1$-$C_2$)alkyl, wherein the substituents are up to three independently selected from halogen, ($C_1$-$C_6$)alkoxy, cyano or trifluoromethyl; carboxy or an agronomically acceptable salt thereof, ($C_1$-$C_6$)alkoxycarbonyl or phenyl group;

X is a fluoro, bromo, chloro or iodo atom;

Y is a hydrogen, fluoro, bromo, iodo, ($C_1$-$C_6$)alkyl, ($C_3$-$C_8$)cycloalkyl, carboxy, or agronomically acceptable salts thereof, ($C_1$-$C_6$)alkoxycarbonyl, phenyl($C_1$-$C_6$)alkyl, ($C_2$-$C_6$)alkenyl and ($C_2$-$C_6$)alkynyl group wherein the alkyl, cycloalkyl, phenylalkyl and phenyl group may have up to three substituents each independently selected from the group consisting of halogen, trifluoromethyl, cyano and ($C_1$-$C_6$)alkoxy groups; and B is hydrogen, carboxy or an agronomically acceptable salt thereof, ($C_1$-$C_6$)alkoxycarbonyl, methylene (=$CH_2R^4$) or $CZZ^1Z^2$ group wherein $R^4$ is a ($C_1$-$C_6$)alkyl or ($C_2$-$C_6$)alkenyl group and Z, $Z^1$ and $Z^2$ are each independently a hydrogen, fluoro, bromo, chloro or iodo atom; provided that for any one molecule X, Y, Z, $Z^1$ and $Z^2$ are not all hydrogen atoms.

3. The compound of claim 2 wherein $R^1$ is hydrogen, ($C_1$-$C_6$)alkyl, ($C_3$-$C_8$)cycloalkyl, an alkali metal cation, a sulfonium cation, ammonium cation or mono, di or tri($C_1$-$C_4$)alkyl ammonium cation;

$R^2$ and $R^3$ are each independently hydrogen, a carboxy or an agronomically acceptable salt thereof or ($C_1$-$C_2$)alkyl group which may be optionally substituted with up to one substituent selected from fluoro, chloro, bromo, iodo, ($C_1$-$C_2$)alkoxy, cyano or trifluoromethyl group;

X is a fluoro, bromo or chloro atom;

Y is a hydrogen, carboxy or an alkali metal or ammonium salt thereof or ($C_1$-$C_6$)alkoxycarbonyl group; and B is hydrogen or $CZZ^1Z^2$ wherein Z, $Z^1$ and $Z^2$ are each independently a hydrogen, fluoro, bromo or chloro atom.

4. The compound of claim 3 wherein $R^1$ is hydrogen, ($C_1$-$C_2$)alkyl, ($C_1$-$C_2$)sulfonium or a cation selected from sodium, potassium, ammonium or ($C_1$-$C_2$)alkyl substituted ammonium;

$R^2$ is hydrogen;

$R^3$ is hydrogen, methyl or ethyl group;

X is a bromo or chloro atom;

Y is hydrogen, bromo, chloro, methoxy, ethoxy or carboxy group or an alkali metal or ammonium salt thereof; and B is a hydrogen atom or $CZZ^1Z^2$ wherein Z and $Z^1$ are hydrogen atoms and $Z^2$ is a bromo or chloro atom.

5. The compound of claim 4 wherein $R^1$ is hydrogen, ($C_1$-$C_2$)alkyl group or a cation selected from sodium, potassium, ammonium and diethyl ammonium;

$R^2$ and $R^3$ are hydrogen atoms;

X is a bromo or chloro atom;

Y is a hydrogen, bromo or chloro atom; and

B is hydrogen or $CZZ^1Z^2$ where Z and $Z^1$ are hydrogen atoms and $Z^2$ is a bromo or chloro atom.

6. The compound of claim 4 selected from the group consisting of beta-bromoethylidene-aminooxyacetic acid, beta-chloroethylidene-aminooxyacetic acid, beta-bromoethylidene-alpha-aminooxypropionic acid, beta-chloroethylidene-alpha-aminooxypropionic acid and a sodium, potassium or ammonium salt thereof.

7. A herbicidal composition comprising the compound of claim 2 in a herbicidally effective amount and an agronomically acceptable carrier.

8. A herbicidal composition comprising the compound of claim 3 in a herbicidally effective amount and an agronomically acceptable carrier.

9. A herbicidal composition comprising the compound of claim 5 in a herbicidally effective amount and an agronomically acceptable carrier.

10. A method for combatting weeds comprising applying to the surface of the growth medium through which the weeds are to emerge or to the weeds a herbicidally effective amount of a compound of the formula

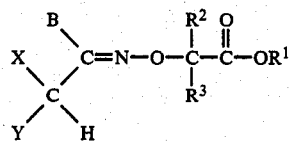

wherein
R$^1$ is hydrogen; (C$_1$-C$_6$)alkyl; (C$_3$-C$_8$)cycloalkyl; ((C$_1$-C$_3$)alkoxy)$_n$(C$_1$-C$_6$)alkyl, ((C$_1$-C$_3$)alkoxy)$_n$aryl, wherein n is 0 or 1 and the aryl may be substituted with up to three substituents each independently selected from halogen, (C$_1$-C$_6$)alkoxy, cyano and trifluoromethyl groups; phenyl(C$_1$-C$_6$)alkyl, aryl, or agronomically acceptable cations;

R$^2$ and R$^3$ are each independently hydrogen, optionally substituted (C$_1$-C$_6$)alkyl, optionally substituted (C$_3$-C$_8$)cycloalkyl, optionally substituted phenyl(C$_1$-C$_2$)alkyl, wherein the substituents are up to three independently selected from halogen, (C$_1$-C$_6$)alkoxy, cyano or trifluoromethyl group, carboxy or an agronomically acceptable salt thereof, (C$_1$-C$_6$)alkoxycarbonyl or phenyl group;

X is a hydrogen, fluoro, bromo, chloro or iodo atom;

Y is hydrogen, fluoro, bromo, iodo(C$_1$-C$_6$)alkyl, (C$_3$-C$_8$)cycloalkyl, carboxy or agronomically acceptable salts thereof, (C$_1$-C$_6$)alkoxycarbonyl, phenyl(C$_1$-C$_6$)alkyl, (C$_2$-C$_6$)alkenyl, (C$_2$-C$_6$)alkynyl or a phenyl group optionally substituted with up to three substituents independently selected from halogen, trifluoromethyl, (C$_1$-C$_6$)alkoxy, nitro, (C$_1$-C$_6$)alkoxycarbonyl, (C$_1$-C$_6$)alkyl and aryl and wherein Y is an alkyl, cycloalkyl or phenylalkyl group it may be substituted with up to three substituents independently selected from halogen, trifluoromethyl, cyano and (C$_1$-C$_6$)alkoxy group; and B is hydrogen, carboxy or agronomically acceptable salts thereof, (C$_1$-C$_6$)alkoxycarbonyl, methylene (—CH$_2$R$^4$) or CZZ$^1$Z$^2$ group wherein R$^4$ is a (C$_1$-C$_6$)alkyl or (C$_2$-C$_6$)alkenyl group and Z, Z$^1$ and Z$^2$ are each independently a hydrogen, fluoro, bromo, chloro or iodo atom.

11. The method of claim 10 wherein R$^1$ is hydrogen, (C$_1$-C$_2$)alkyl, (C$_1$-C$_2$)sulfonium or a cation selected from sodium, potassium, ammonium or (C$_1$-C$_2$)alkyl substituted ammonium; R$^2$ is hydrogen; R$^3$ is hydrogen, methyl or ethyl group; X is a bromo or chloro atom; Y is hydrogen, bromo, chloro, methoxy, ethoxy or carboxy group or an alkali metal or ammonium salt thereof; and B is a hydrogen atom or CZZ$^1$Z$^2$ wherein Z and Z$^1$ are hydrogen atoms and Z$^2$ is a bromo or chloro atom.

12. The method of claim 11 wherein R$^1$ is hydrogen, (C$_1$-C$_2$)alkyl group or a cation selected from sodium, potassium, ammonium and diethyl ammonium; R$^2$ and R$^3$ are hydrogen atoms; X is a bromo or chloro atom; Y is a hydrogen, bromo or chloro atom; and B is hydrogen or CZZ$^1$Z$^2$ where Z and Z$^1$ are hydrogen atoms and Z$^2$ is a bromo or chloro atom.

13. The method of claim 12 wherein the growth medium is soil and the compound is applied to the soil before the weeds emerge through the soil.

* * * * *